(12) United States Patent
Miller (10) Patent No.: US 8,078,420 B2
(45) Date of Patent: Dec. 13, 2011

(54) RAMAN SPECTROMETRY AUTHENTICATION

(76) Inventor: Gary L. Miller, Gainesville, FL (US)

(*) Notice: Subject to any disclaimer, the term of this patent is extended or adjusted under 35 U.S.C. 154(b) by 303 days.

(21) Appl. No.: 11/976,184

(22) Filed: Oct. 22, 2007

(65) Prior Publication Data

US 2008/0189066 A1 Aug. 7, 2008

Related U.S. Application Data (60) Provisional application No. 60/858,956, filed on Nov. 15, 2006.

(51) Int. Cl.
*G01N 37/00* (2006.01)

(52) U.S. Cl. ............ 702/82; 252/301.36; 257/761

(58) Field of Classification Search .......... 702/19, 702/20, 30, 32, 66, 75, 82, 85, 104, 182, 702/183; 252/301.36; 257/761; 235/492; 250/252.1; 356/71, 73, 301; 435/6; 436/518, 436/525; 506/6; 546/23
See application file for complete search history.

(56) References Cited

U.S. PATENT DOCUMENTS

| | | | |
|---|---|---|---|
| 5,149,812 A | 9/1992 | Thevignot | |
| 5,763,176 A | 6/1998 | Slater et al. | |
| 5,866,430 A | 2/1999 | Grow | |
| 6,002,471 A | 12/1999 | Quake | |
| 6,008,888 A | 12/1999 | Nottke et al. | |
| 6,180,415 B1 | 1/2001 | Schultz et al. | |
| 6,770,488 B1 | 8/2004 | Carron et al. | |
| 6,781,690 B2 | 8/2004 | Armstrong et al. | |
| 6,835,326 B2 * | 12/2004 | Barbera-Guillem | 252/301.36 |
| 6,995,839 B1 | 2/2006 | Shapiro | |
| 7,001,721 B1 | 2/2006 | Whitcombe et al. | |
| 2003/0235836 A1 | 12/2003 | Simonetta et al. | |
| 2005/0156318 A1* | 7/2005 | Douglas | 257/761 |

OTHER PUBLICATIONS

Ira Steiner, "Super Bowl Footballs Get Laser Treatment", AuctionBytes.com, Feb. 4, 2002.

* cited by examiner

*Primary Examiner* — John H Le
(74) *Attorney, Agent, or Firm* — Larson & Larson, P.A.; Frank Liebenow; Justin P. Miller (57) ABSTRACT

A method and apparatus for authenticating items having a security mark containing a DNA fragment to prevent fraud uses a Raman spectrometer to generate a response spectrum from monochrome incident beam on the security mark on an item. Gross fluorescence is removed from the security mark response spectrum to produce a Raman security mark response spectrum. Peaks in the Raman security mark response spectrum are detected to generate Raman security mark peak data. The Raman security mark peak data is compared to a Raman peak library to determine if there is a match. The item is indicated as being authentic if a match of the Raman security mark peak data is found in the Raman peak library.

15 Claims, 10 Drawing Sheets

| wave num. | average l | upper l | lower l | st dev l | average f | upper f | lower f | st dev f | average v | upper v | lower v | st dev v |
|---|---|---|---|---|---|---|---|---|---|---|---|---|
| 200 | 0.062765 | 0.078344 | 0.047186 | 0.007789 | 0.049912 | 0.052116 | 0.047709 | 0.001102 | 0.049734 | 0.0608 | 0.038668 | 0.005533 |
| 203.125 | 0.069983 | 0.086691 | 0.053276 | 0.008354 | 0.055721 | 0.058029 | 0.053414 | 0.001154 | 0.055052 | 0.066908 | 0.043196 | 0.005928 |
| 206.25 | 0.07893 | 0.096702 | 0.061159 | 0.008886 | 0.063003 | 0.065534 | 0.060472 | 0.001265 | 0.061568 | 0.074087 | 0.04905 | 0.006259 |
| ******** | ******** | ******** | ******** | ******** | ******** | ******** | ******** | ******** | ******** | ******** | ******** | ******** |
| 350 | 0.635105 | 0.683415 | 0.586794 | 0.024155 | 0.545515 | 0.582527 | 0.508504 | 0.018506 | 0.491897 | 0.507331 | 0.476463 | 0.007717 |
| 353.125 | 0.641982 | 0.690959 | 0.593004 | 0.024489 | 0.551249 | 0.588549 | 0.513949 | 0.01865 | 0.497157 | 0.512801 | 0.481514 | 0.007822 |
| 356.25 | 0.648961 | 0.698662 | 0.59926 | 0.02485 | 0.557127 | 0.594714 | 0.51954 | 0.018793 | 0.502481 | 0.518299 | 0.486663 | 0.007909 |
| ******** | ******** | ******** | ******** | ******** | ******** | ******** | ******** | ******** | ******** | ******** | ******** | ******** |
| 1225 | 0.999766 | 1.000364 | 0.999169 | 0.000299 | 0.997633 | 0.999463 | 0.995803 | 0.000915 | 0.992402 | 0.999641 | 0.985163 | 0.003619 |
| 1228.125 | 0.999925 | 1.000131 | 0.999718 | 0.000103 | 0.998712 | 1.000122 | 0.997303 | 0.000705 | 0.993616 | 1.00049 | 0.986742 | 0.003437 |
| 1231.25 | 0.999734 | 1.00037 | 0.999098 | 0.000318 | 0.999462 | 1.000467 | 0.998456 | 0.000503 | 0.994666 | 1.001126 | 0.988205 | 0.00323 |
| 1234.375 | 0.999233 | 1.000457 | 0.998008 | 0.000612 | 0.999826 | 1.000378 | 0.999273 | 0.000276 | 0.995542 | 1.001592 | 0.989491 | 0.003025 |
| 1237.5 | 0.998502 | 1.000329 | 0.996675 | 0.000913 | 0.999833 | 1.000102 | 0.999565 | 0.000134 | 0.996187 | 1.001877 | 0.990497 | 0.002845 |
| 1240.625 | 0.9976 | 0.999913 | 0.995286 | 0.001157 | 0.99956 | 1.000419 | 0.998701 | 0.00043 | 0.996538 | 1.001949 | 0.991128 | 0.002705 |
| 1243.75 | 0.996606 | 0.999237 | 0.993974 | 0.001316 | 0.999035 | 1.000412 | 0.997658 | 0.000689 | 0.996736 | 1.001988 | 0.991484 | 0.002626 |
| 1246.875 | 0.99551 | 0.99832 | 0.992699 | 0.001405 | 0.998272 | 0.999987 | 0.996558 | 0.000857 | 0.996846 | 1.002068 | 0.991624 | 0.002611 |
| 1250 | 0.994282 | 0.997251 | 0.991312 | 0.001485 | 0.997335 | 0.999422 | 0.995248 | 0.001044 | 0.996873 | 1.002096 | 0.99165 | 0.002611 |
| ******** | ******** | ******** | ******** | ******** | ******** | ******** | ******** | ******** | ******** | ******** | ******** | ******** |
| 3387.5 | 0.002446 | 0.003608 | 0.001284 | 0.000581 | 0.002721 | 0.004395 | 0.001048 | 0.000837 | 0.003143 | 0.004421 | 0.001864 | 0.000639 |
| 3390.625 | 0.002341 | 0.00357 | 0.001112 | 0.000615 | 0.002747 | 0.004675 | 0.00082 | 0.000964 | 0.003034 | 0.004241 | 0.001827 | 0.000604 |
| 3393.75 | 0.002264 | 0.003552 | 0.000977 | 0.000644 | 0.002822 | 0.005089 | 0.000554 | 0.001134 | 0.002985 | 0.004218 | 0.001753 | 0.000616 |
| 3396.875 | 0.002259 | 0.003599 | 0.000919 | 0.00067 | 0.002884 | 0.005282 | 0.000486 | 0.001199 | 0.00302 | 0.004315 | 0.001725 | 0.000648 |

FIG. 8

| wn | 4str mean | stdev | aaaa mean | stdev | vwa mean | stdev | lpl mean | stdev | fttt mean | stdev | f13b mean | stdev | cgcg | cgcg | efes | efes |
|---|---|---|---|---|---|---|---|---|---|---|---|---|---|---|---|---|
| 200 | 0.060 | 0.005 | 0.047 | 0.005 | 0.033 | 0.005 | 0.048 | 0.005 | 0.037 | 0.005 | 0.065 | 0.007 | 0.03 | 0.03 | 0.03 | 0.04 |
| 203.125 | 0.067 | 0.006 | 0.052 | 0.006 | 0.036 | 0.005 | 0.054 | 0.006 | 0.041 | 0.006 | 0.073 | 0.008 | 0.04 | 0.04 | 0.03 | 0.05 |
| 206.25 | 0.076 | 0.007 | 0.058 | 0.006 | 0.039 | 0.006 | 0.062 | 0.006 | 0.047 | 0.007 | 0.083 | 0.009 | 0.04 | 0.04 | 0.04 | 0.05 |
| 350 | 0.508 | 0.039 | 0.461 | 0.019 | 0.310 | 0.028 | 0.428 | 0.038 | 0.325 | 0.045 | 0.498 | 0.039 | 0.32 | 0.33 | 0.31 | 0.35 |
| 353.125 | 0.515 | 0.039 | 0.466 | 0.019 | 0.314 | 0.028 | 0.434 | 0.039 | 0.329 | 0.045 | 0.504 | 0.039 | 0.33 | 0.33 | 0.31 | 0.35 |
| 356.25 | 0.522 | 0.039 | 0.472 | 0.019 | 0.317 | 0.028 | 0.441 | 0.039 | 0.332 | 0.046 | 0.510 | 0.040 | 0.33 | 0.34 | 0.32 | 0.36 |
| 1225 | 0.987 | 0.004 | 0.984 | 0.007 | 0.942 | 0.009 | 0.990 | 0.006 | 0.860 | 0.072 | 0.993 | 0.004 | 0.96 | 0.96 | 0.95 | 0.95 |
| 1228.13 | 0.987 | 0.004 | 0.985 | 0.007 | 0.944 | 0.009 | 0.990 | 0.006 | 0.862 | 0.071 | 0.993 | 0.004 | 0.96 | 0.96 | 0.95 | 0.95 |
| 1231.25 | 0.987 | 0.004 | 0.985 | 0.006 | 0.946 | 0.009 | 0.989 | 0.006 | 0.864 | 0.071 | 0.994 | 0.004 | 0.96 | 0.96 | 0.95 | 0.95 |
| 1234.38 | 0.986 | 0.004 | 0.986 | 0.006 | 0.948 | 0.009 | 0.989 | 0.007 | 0.865 | 0.071 | 0.994 | 0.004 | 0.96 | 0.97 | 0.95 | 0.96 |
| 1237.5 | 0.986 | 0.005 | 0.987 | 0.006 | 0.950 | 0.008 | 0.989 | 0.007 | 0.867 | 0.071 | 0.994 | 0.004 | 0.96 | 0.97 | 0.96 | 0.96 |
| 1240.63 | 0.985 | 0.005 | 0.987 | 0.006 | 0.952 | 0.008 | 0.988 | 0.007 | 0.868 | 0.071 | 0.994 | 0.004 | 0.96 | 0.97 | 0.96 | 0.96 |
| 1243.75 | 0.984 | 0.005 | 0.988 | 0.005 | 0.954 | 0.008 | 0.987 | 0.007 | 0.870 | 0.070 | 0.993 | 0.004 | 0.97 | 0.97 | 0.96 | 0.96 |
| 1246.88 | 0.983 | 0.005 | 0.989 | 0.005 | 0.956 | 0.008 | 0.987 | 0.008 | 0.871 | 0.070 | 0.993 | 0.004 | 0.97 | 0.97 | 0.96 | 0.96 |
| 1250 | 0.983 | 0.005 | 0.990 | 0.005 | 0.958 | 0.007 | 0.986 | 0.008 | 0.873 | 0.070 | 0.993 | 0.004 | 0.97 | 0.97 | 0.96 | 0.96 |
| 3387.5 | 0.011 | 0.002 | 0.008 | 0.002 | 0.010 | 0.004 | 0.010 | 0.002 | 0.021 | 0.003 | 0.013 | 0.003 | 0.01 | 0.01 | 0.01 | 0.02 |
| 3390.62 | 0.011 | 0.002 | 0.008 | 0.002 | 0.009 | 0.004 | 0.010 | 0.002 | 0.021 | 0.003 | 0.013 | 0.003 | 0.01 | 0.01 | 0.01 | 0.02 |
| 3393.75 | 0.011 | 0.002 | 0.008 | 0.002 | 0.009 | 0.004 | 0.009 | 0.002 | 0.021 | 0.003 | 0.013 | 0.003 | 0.01 | 0.01 | 0.01 | 0.02 |
| 3396.88 | 0.011 | 0.002 | 0.008 | 0.002 | 0.009 | 0.004 | 0.009 | 0.002 | 0.020 | 0.003 | 0.013 | 0.003 | 0.02 | 0.00 | 0.01 | 0.00 |

| Peak No. | Wave Number | Intensity | Std. Dev |
|---|---|---|---|
| 1 | 490 | 0.80 | x1 |
| 2 | 580 | 0.65 | x2 |
| 3 | 690 | 0.30 | x3 |
| ******* | ********* | ******* | ******** |
| 7 | 1100 | 0.65 | x7 |
| 8 | 1150 | 0.98 | x8 |
| 9 | 1200 | 0.95 | x9 |
| ****** | ******* | ****** | ******* |
| 15 | 1600 | 1.15 | x15 |
| 16 | 1650 | 0.20 | x16 |
| ******* | ********* | ******* | ******* |
| 31 | 2420 | -0.15 | x31 |

RAMAN SPECTROMETRY AUTHENTICATION

CROSS-REFERENCE TO RELATED APPLICATIONS

This application is related to U.S. Provisional Patent Application No. 60/858,956 filed Nov. 15, 2006 and which is expressly incorporated herein in its entirety.

BACKGROUND OF THE INVENTION

The present invention relates to apparatus and methods for authenticating items such as documents, cards, currency or other objects using difficult-to-forge markings on the items.

The prior art uses many different difficult-to-forge markings on items to thwart counterfeiting, forgery, frauds, identity theft, security violations. Marked items include documents such as bank documents and legal papers, cards such as credit cards and identification cards, currency, works of art, memorabilia and other valuable items. Some marking techniques use substances such as ink which contains an unique material not apparent to visual observation but can be detected by a special process or equipment.

One unique material used in marking items includes DNA (deoxyribonucleic acid) fragments derived from human, animal or plant sources. The DNA can be identified by processes similar to those used to identify a perpetrator from DNA found at a crime scene or used to identify a genetic disease of a patient. Such processes usually include extraction of the DNA and amplification by polymerase chain reaction. The amplified DNA is detected using electrophoresis, attachment of a radioactive or fluorescent marker, and/or reaction within cells of a microchip. These processes are performed in a laboratory and generally require long time periods as well as destruction of at least a portion of the marking material.

Spectrometry such a Raman spectrometry can be employed to rapidly identify certain materials which have a relatively high Raman response and low fluorescence. DNA is characterized by a relatively low Raman response and high fluorescence and thus is generally considered unsuited for identification by Raman spectrometry. Surface enhanced Raman spectrometry (SERS) wherein a roughened metal surface or metal colloid increases the Raman response is employed to identify certain abnormal DNA associated with disease.

BRIEF SUMMARY OF THE INVENTION

The invention is summarized in a method and apparatus for authenticating items having a security mark containing a DNA fragment to prevent fraud wherein a Raman spectrometer generates a response spectrum of a security mark on an item, gross fluorescence is removed from the security mark response spectrum to produce a Raman security mark response spectrum, peaks in the Raman security mark response spectrum are detected to generate Raman security mark peak data, the Raman security mark peak data is compared to a Raman peak library to determine if there is a match, and the item is indicated as being authentic if a match of the Raman security mark peak data is found in the Raman peak library. It has been found that a DNA containing mark can be authenticated in spite of the low Raman response and the high fluorescence.

Additionally the security mark response spectrum can be compared with a library of response spectrums of DNA fragments to determine if the security mark response spectrum is acceptable prior to removing gross fluorescence from the security mark response spectrum.

Many techniques can be used for comparing of the security mark response spectrum to the library of response spectrums but in one example intensity values of the security mark response are compared with upper and lower limit values in the library of response spectrums.

Many techniques for removing fluorescence from the intensity values can be employed including determining an average value of intensity data within a section surrounding each point of the security mark response spectrum, and subtracting the average value from each point to produce the Raman security mark spectrum. Another example uses forward and reverse Fourier transform methods to filter fluorescence values from the intensity data.

In one embodiment the comparing of Raman peak data with the Raman peak library includes comparing wave numbers of each peak with wave numbers in the Raman peak library and comparing intensity values of each peak with intensity values in the Raman peak library.

BRIEF DESCRIPTION OF THE DRAWINGS

FIG. 8 is a table illustrating portions of a first possible condensed fluorescence library in the system of FIG. 2.

DETAILED DESCRIPTION OF THE INVENTION

Figure 1:
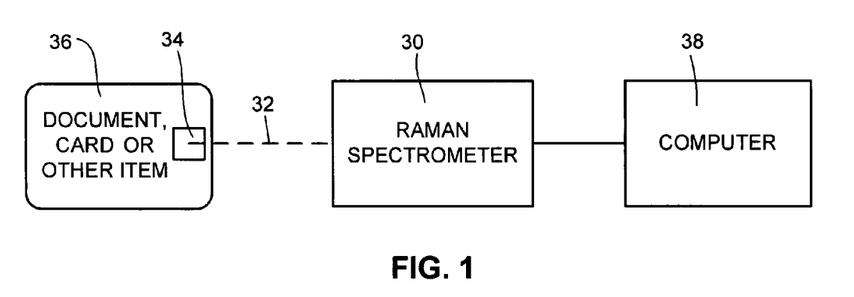
FIG. 1 is a block diagram of an item authentication system in accordance with the invention.

In a system shown in FIG. 1 for authenticating items, a Raman spectrometer 30 generates a monochromatic light beam 32 directed against a security mark 34 on a document, card or other item 36. The security mark 34 contains a quantity of at least one type of DNA (deoxyribonucleic acid) fragment which is difficult to forge. Light from the security mark 34 is received by the Raman spectrometer 30 which detects a spectrum of the light and passes the spectrum data to a microprocessor, embedded processor, or computer 38 (hereinafter referred to as computer) for processing to authenticate or indicate the non-authenticity of the item.

One suitable mark is describe in United States Patent Application Publication No. 2003/0235836 which publication is expressly incorporated herein in its entirety. This document discloses production of polymer beads, of 0.5 to 50 microns in diameter, in which are encapsulated replications of one or more DNA fragments, preferably selected from polymorphic fragments such as STR (short tandem repeats—also known as microsatellite) fragments or SNP (single nucleotide polymorphism) fragments. These beads can be suspended in a fluid or ink which can be applied to authentic items by pen, brush, printer or presses or can otherwise be incorporated in the items in either a visible or non-visible form. One characteristic of polymorphic DNA fragments is that the fragments are difficult to duplicate without knowing their end sequences for attachment of primers to enable PCR replication. Since there are a very large number of different polymorphic segments or fragments in human DNA, it is very difficult to determine which DNA fragment or fragments are included and thus the DNA sequence or sequences are unknown except to the manufacturer and very difficult to determine particularly where several fragments are employed. Thus it is very difficult to forge a mark with DNA fragments.

Figure 2:
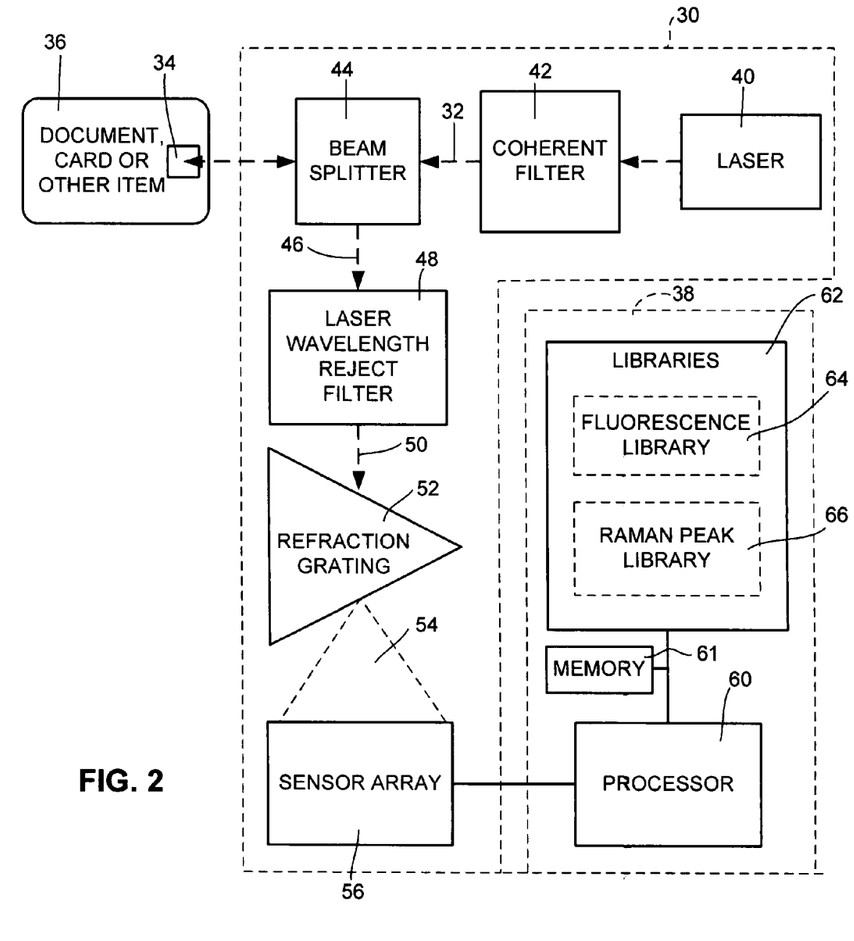
FIG. 2 is a more detailed block diagram of the system of FIG. 1.
Figure 4:
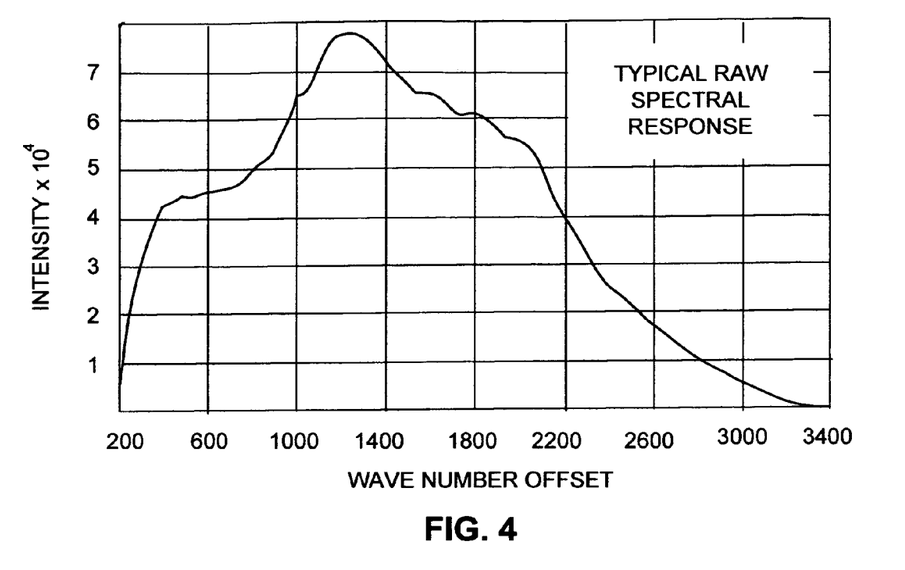
FIG. 4 is a graph of typical raw data from a Raman spectrometer in FIG. 2

As shown in FIG. 2, a typical Raman spectrometer 30 includes a laser 40 and coherent filter 42 for generating the monochromatic light beam 42. A beam splitter 44 such as a half silvered mirror reflects the light 46 from the mark 34 to a filter 48 which removes the frequency component of the laser frequency. The remaining light 50 from the filter 48 is refracted such as by a refraction grating (illustrated as prism 52) into a light spectrum 54 which is applied to a sensor array 56. The intensity values of different frequencies in the spectrum 54 are detected in individual elements of the sensor array 56 and output to the computer 38. In one embodiment, the laser 40 is a green laser at 532 nm (wave number=18796 $cm^{-1}$) with a power output of up to 100 mW, the sensor array 56 is a 1024 linear CCD and the spectrum 54 being sensed ranges from about 538 nm to about 649 nm (18596 $cm^{-1}$ to 15400 $cm^{-1}$ in steps of 3.125 $cm^{-1}$). The graph in FIG. 4 represents intensity readings taken with the laser set at 6 mW and an exposure of about 4 seconds; the abscissa is expressed in offset wave number ($cm^{-1}$) from the wave number of the incident radiation.

Figure 3:
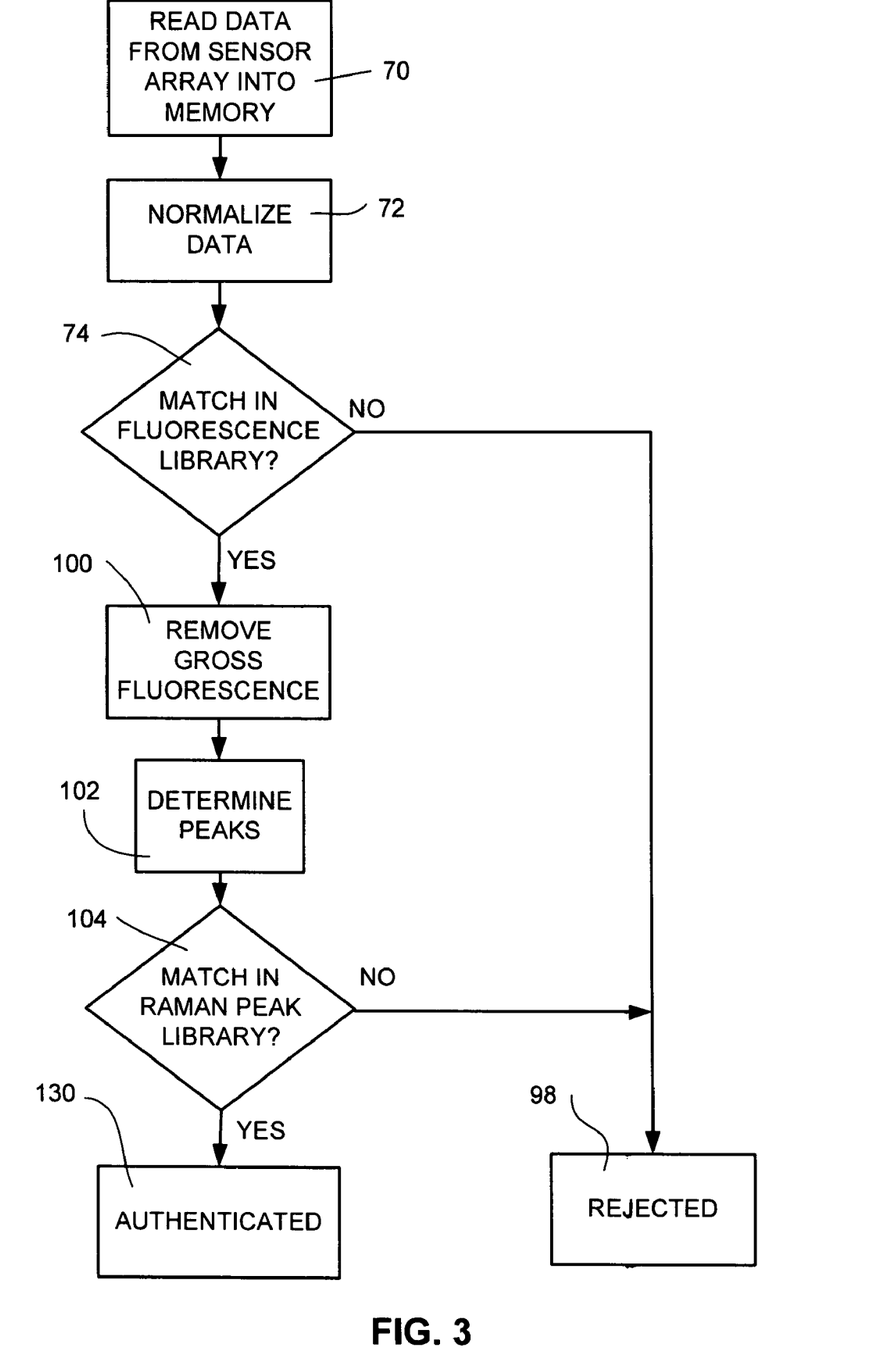
FIG. 3 is a step diagram of the program employed in a computer of FIG. 2 to authenticate items.
Figure 5:
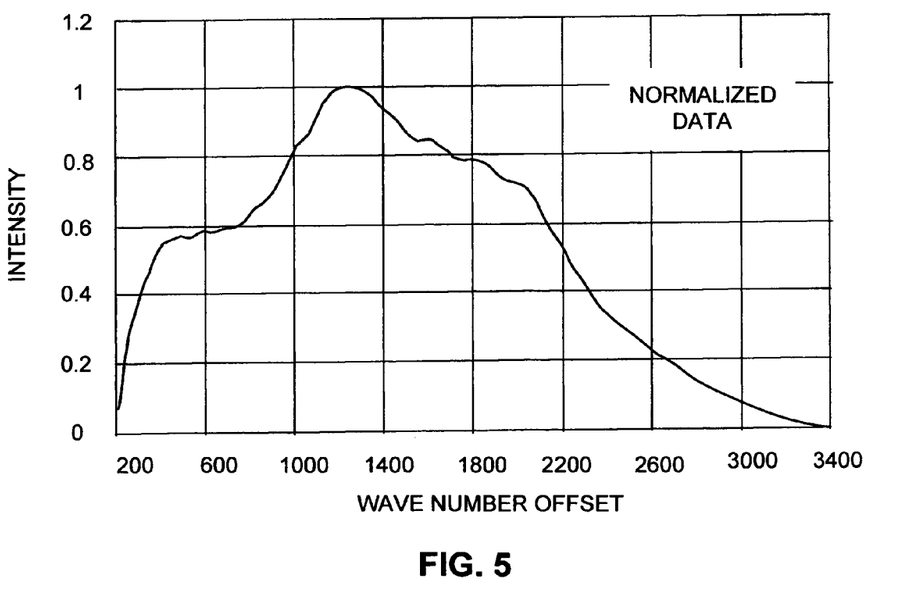
FIG. 5 is a graph of normalized data derived from the data of FIG. 4

Computer 38 includes a processor 60 with associated memory 61 and libraries 62 including a fluorescence library 64 and a Raman peak library 66. The program for the processor 60 is illustrated in FIG. 3 wherein the data from the sensor array 56 is read in step 70 into memory 61 and normalized in step 72. The graph of FIG. 5 illustrated normalized data from FIG. 4. A typical source algorithm for normalizing data is as follows:

```
Dim NormData(1023) As Double
Dim Matches(15) As String
StartI = 1    'Start of raw data
EndI = 1024 'length of raw data
ColWn = 1    'wave number column
ColY = 2     'intensity column
'
ymax = 0
For I = StartI To EndI         'find maximum
    datum = Cells(I, ColY)
    If datum > ymax Then ymax = datum
Next I
j = o
For I = StartI To EndI         'normalize data
    NormData(j) = Cells(I, ColY) / ymax   'store in local match array
```

```
    j = j + 1
Next I
'
```

Figure 6:
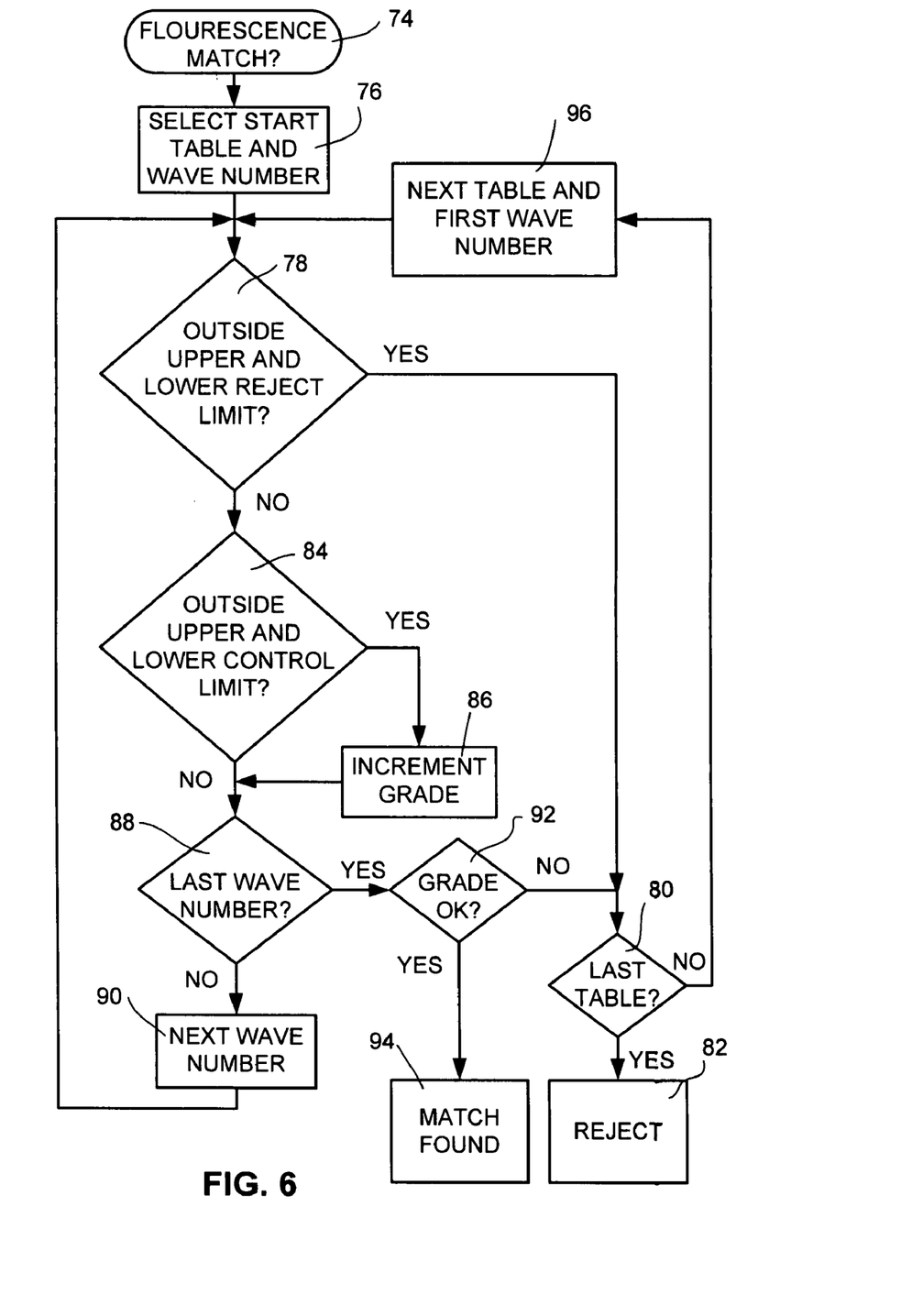
FIG. 6 is a step diagram of a procedure for determining a match of a spectrum generated by the spectrometer with spectrum data in a fluorescence library.
Figure 7:
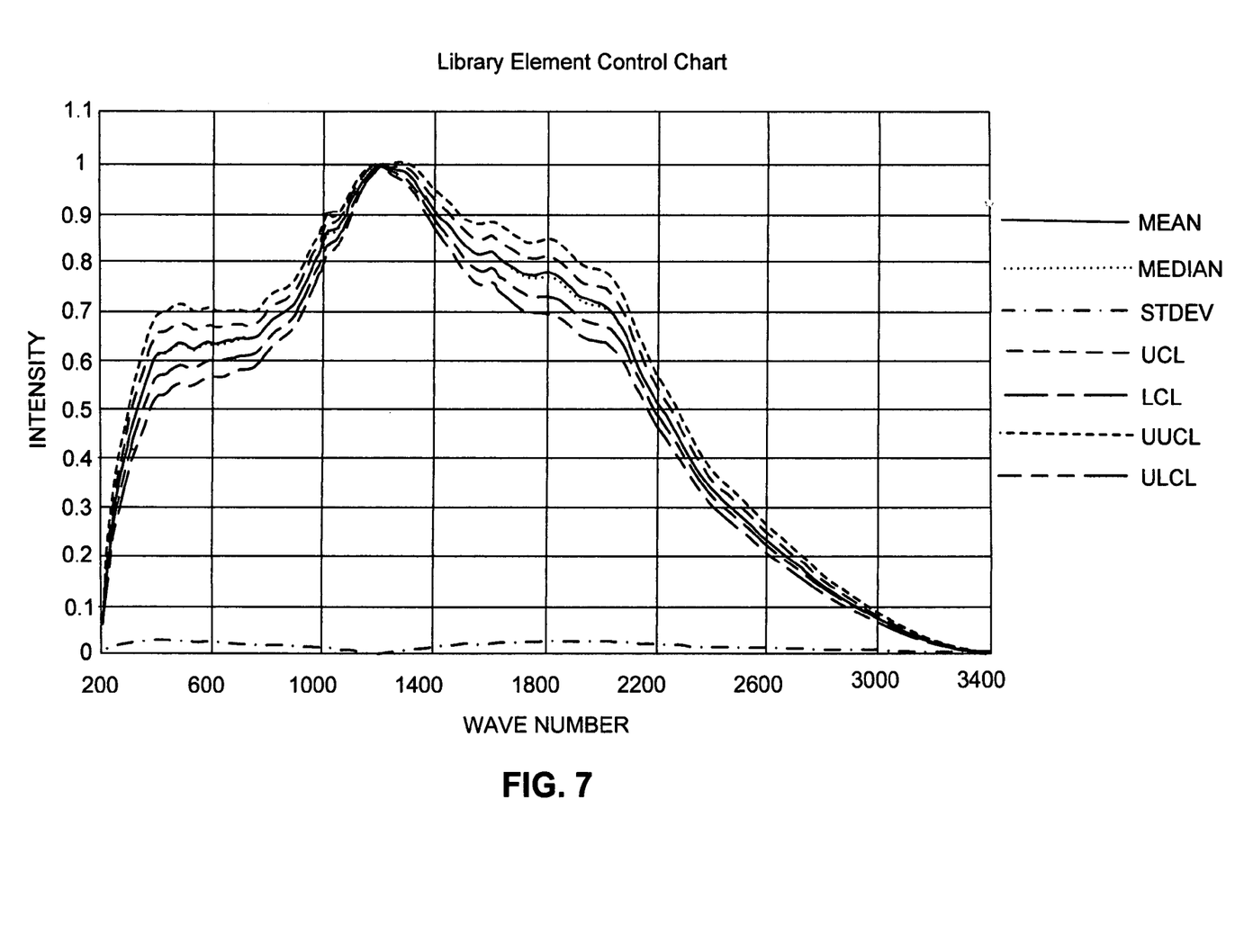
FIG. 7 is a graph illustrating comparison limits employed in a procedure of FIG. 6.

In step 74, the procedure of FIG. 6 is called to determine to initially determine if a match exists in the fluorescence library.

Figure 9:
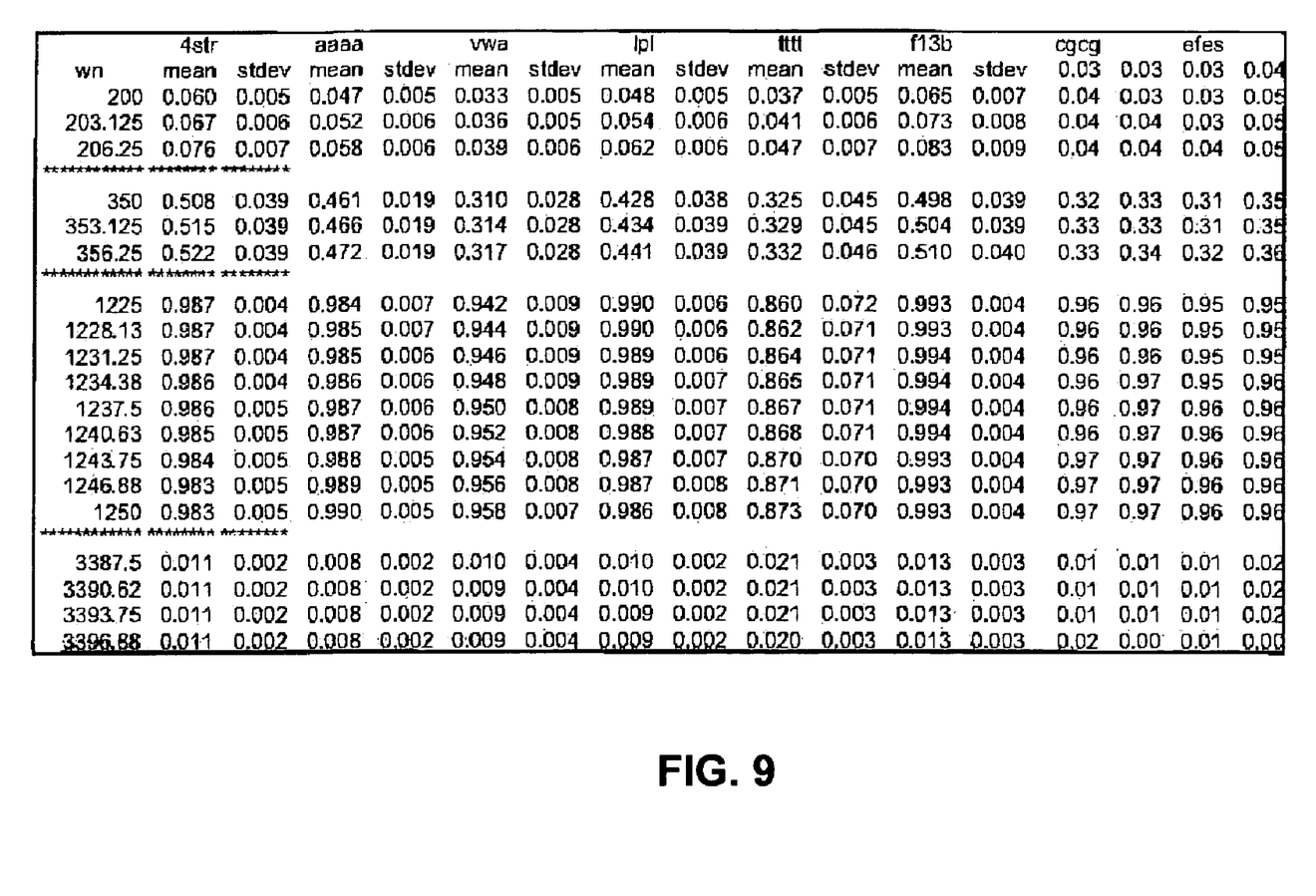
FIG. 9 is a table illustrating portions of a second possible condensed fluorescence library in the system of FIG. 2.

Typical fluorescence libraries are illustrated in FIGS. 8 and 9 (only a few of the 1024 data points or rows shown). In FIG. 8, column "average I" contains the normalized average intensity readings of a mark I containing first fragments of DNA, column "upper I" contains the highest permissible normalized intensity readings of the mark I, the column "lower I" contains the lowest permissible normalized intensity readings and column "st dev I" contains normal deviation values; columns "average f", "upper f", "lower f" and "st dev f" contain similar normalized intensity readings, highest permissible normalized readings, lowest permissible normalized readings for a mark f which contains second DNA fragments different from the first DNA fragments; similar additional columns are for additional marks with further different DNA fragments. The library in FIG. 9 differs in that only mean intensity values and standard deviation values are set forth in columns for several different marks with different DNA fragments.

In step 76 of FIG. 6, a table (set of four columns in FIG. 8; set of two columns in FIG. 9) is selected and the first wave number is selected. Step 78 compares the intensity value of the current wave number for the mark undergoing testing for authentication with upper and lower reject limits. For the tables in FIG. 8 the upper and lower reject limits are the columns labeled "upper" and "lower". The following algorithm is employed for the tables of FIG. 9:

```
NLen=1024              'number of data points
IDRow = 1              'Data ID is in (IDRow, MeanCol)
DataStartRow = 3       'first data row after IDs
WnCol = 1              'wave number column
MeanCol = 2            'mean
StdCol = 3             'standard deviation
NSigma = 1.5           'width of acceptance band
NMatch = -1            'number of matches found
For I = 1 To NLibEntry       'cover all library entries
    j = 0
    cond = True
    Do While j < NLen And cond = True
        If Abs(NormData(j) – Cells(j + DataStartRow, MeanCol)) >
            NSigma * Cells(j +
DataStartRow, StdCol) Then cond = False
        j = j + 1
    Loop
    If cond = True Then
        NMatch = NMatch + 1
        Matches(NMatch) = Cells(IDRow, MeanCol) 'place
            matching id into array
    End If
    MeanCol = MeanCol + LibWidth
    MedianCol = MedianCol + LibWidth
    StdCol = StdCol + LibWidth
Next I
Windows(DataWorkBook).Activate
Worksheets(DataWorkSheet).Activate
If NMatch > –1 Then
    For I = 0 To NMatch
        Cells(I + 1, 3) = Matches(I)
    Next I
    MsgBox "Matches found"
Else
    MsgBox "no match"
```

-continued

```
End If
End Sub
```

This algorithm uses a factor "NSigma" which extends the standard deviation to provide the outside upper and lower reject limits. If the normalized intensity value is outside the upper and lower limits, the procedure branches to step 80 where it is determined if the current table (columns) is the last table in the library and if so the mark under test is rejected in step 82.

When step 78 finds the value under test within the upper and lower reject limits, step 84 determines if the value under consideration is within upper and lower control limits. This can be done with an algorithm similar to that listed above for use with the library of FIG. 9 except that the factor "NSigma" is 1 so that the standard deviation value is not extended. If the value under consideration is outside the control limits, step 86 increments a grade value. From step 86 or step 84 if false, the procedure in step 88 determines if the value under consideration is for the last wave number and, if not, step 90 points to the next wave number followed by step 78 where testing of the intensity value for the nest wave number is repeated. When the testing reaches the last wave number, step 88 branches to optional step 92 wherein it can be determined if the grade value reached by steps 86 is acceptable. If true the procedure indicates that a match has been found in step 94. When a match is not found and current table being used is not the last table in the library, step 80 branches to step 96 where the next table (set of columns) is selected and step 78 begins testing the intensity values in the newly selected table.

Returning to FIG. 3, when no match is found in the fluorescence library in the procedure of FIG. 6, step 74 branches to step 98 where the computer indicates that the item is not authentic. When a match with a table in the fluorescence library is found by the procedure of FIG. 6, step 100 removes gross fluorescence values from the data stored in the memory 61 to produce a Raman spectrum such as that illustrated by the graph in FIG. 10. The un-enhanced Raman response is on the order of $10^{-7}$ of the incident laser energy and the fluorescence energy returned to the spectrometer is many times the Raman intensity, so it is necessary to remove the fluorescence response to determine the Raman response. This can be accomplished in several different ways including forward and reverse Fourier transform methods. The following algorithm demonstrates another method wherein a centroid average subtraction procedure is employed. Let m be the number of wave bins corresponding to a wave number range (abscissa segment width of data of FIG. 4 or 5). Then $$w_i = y_i - \sum_{j=i-m}^{i+m} \frac{y_j}{2m+1},$$

for $$I = m : 1024 - m$$

where the $w_i$ are the Raman response intensities from the sample target. The $y_i$ may either the raw spectrometer response of FIG. 4 or the normalized spectrometer response of FIG. 5. In the case where m=16, which corresponds to a abscissa range of 50 $cm^{-1}$, the result is the original intensity from which is subtracted an average of a centered moving range spread over 100 $cm^{-1}$. The value for m may be increased to provide less peak information, or decreased to provide more peak information. A correction for the extended negative slope of the fluorescence response is added to shift the zero baseline to correspond to the average of the result between 2400 and 3300 $cm^{-1}$.

Figure 10:
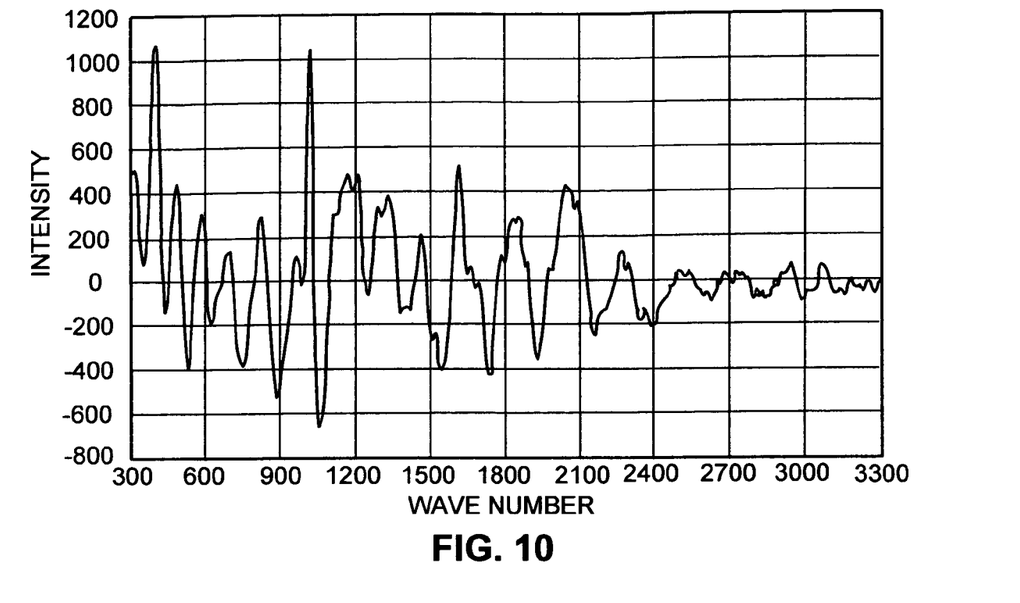
FIG. 10 is a graph illustrating Raman spectrum data after removal of gross fluorescence data from the data of FIG. 4.
Figure 11:
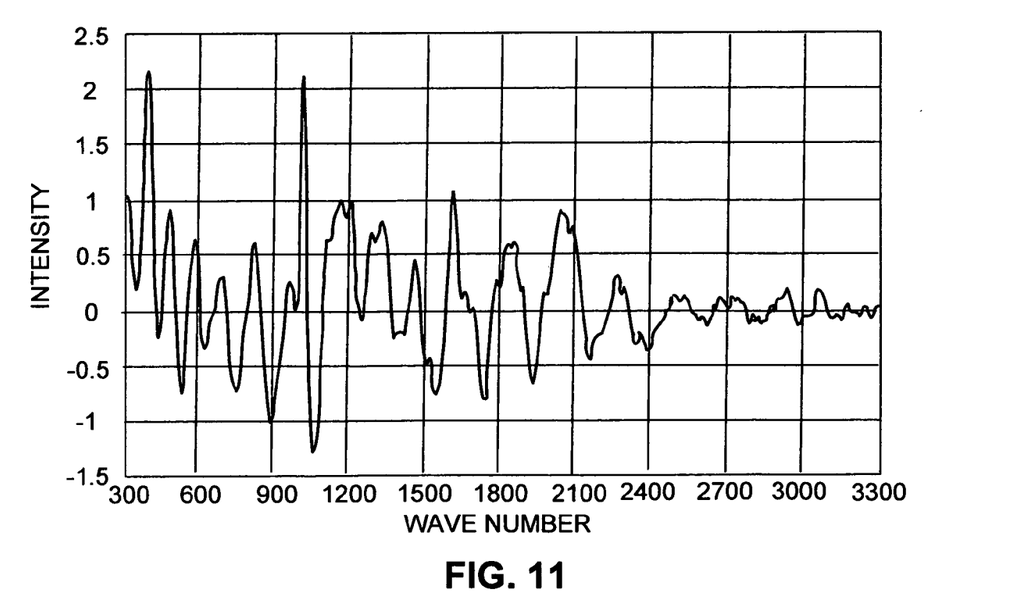
FIG. 11 is a graph illustrating Raman spectrum data after removal of gross fluorescence data from the normalized data of FIG. 5.

FIG. 11 shows the Raman response normalized to the peak intensity values occurring at 1150±50 $cm^{-1}$ as shown in FIG. 10. The Raman response to the encapsulated DNA becomes very clear following the removal of gross fluorescence intensity values. It is noted that the encapsulating polymer has very strong characteristic peaks at 1012 and 1606 $cm^{-1}$.

Figure 12:
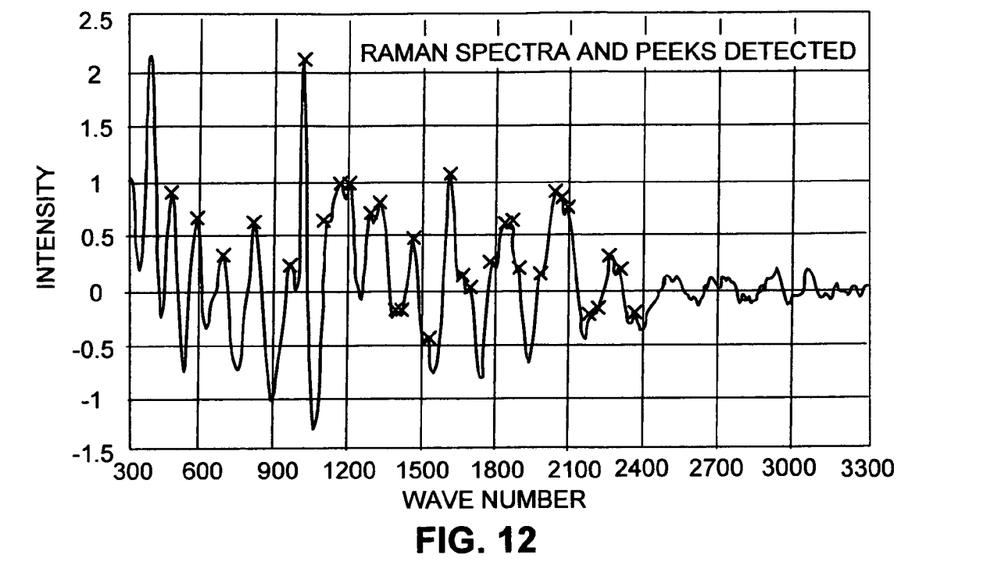
FIG. 12 is a graph of the data of FIG. 11 wherein peaks have been identified.

The automated detection or determination of peaks is the next function performed at 102 in FIG. 3. Because of the characteristics of both the Raman spectrometer (the Bragg fundamental reject filter 48 has some peaks associated with it since it approximates an elliptical band reject filter) the region of interest is limited to 450 to 2400 $cm^{-1}$. Many algorithms exist for peak detection. In this example, the peaks are additionally qualified as follows; the peak must be central located within a certain band of wave number bins, and must be the highest peak in that band. For this example, the chosen band is seven bins wide, or a span of 18.75 $cm^{-1}$. FIG. 12 shows the peaks selected as "*" points superimposed on the original FIG. 11. The wave numbers and intensity values at the peaks become the "fingerprint" of the mark under examination. In FIG. 12, thirty one peaks have been detected, and are used to determine the authenticity of the item being examined.

Figure 13:
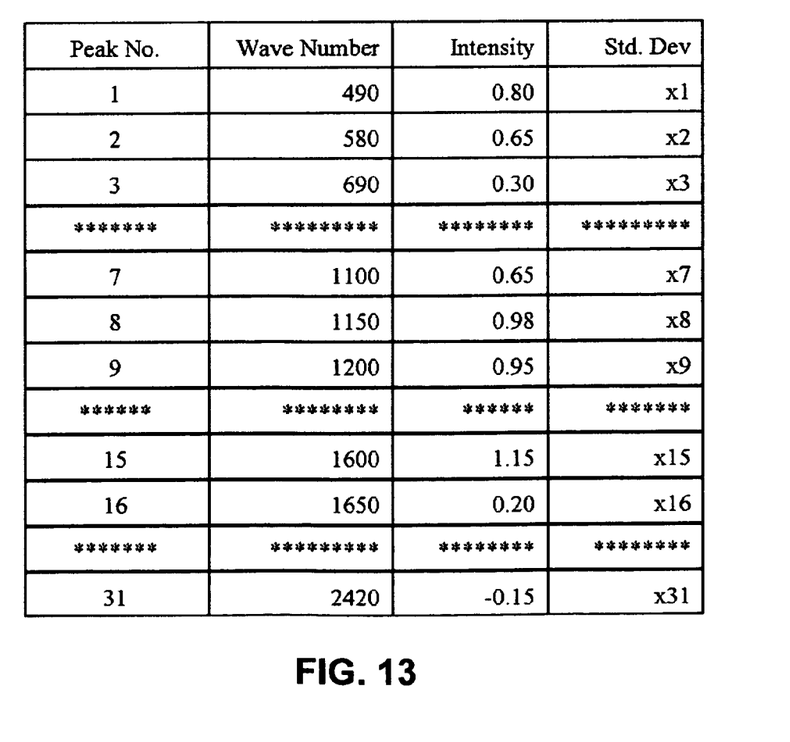
FIG. 13 is a condensed library of Raman peak data.
Figure 14:
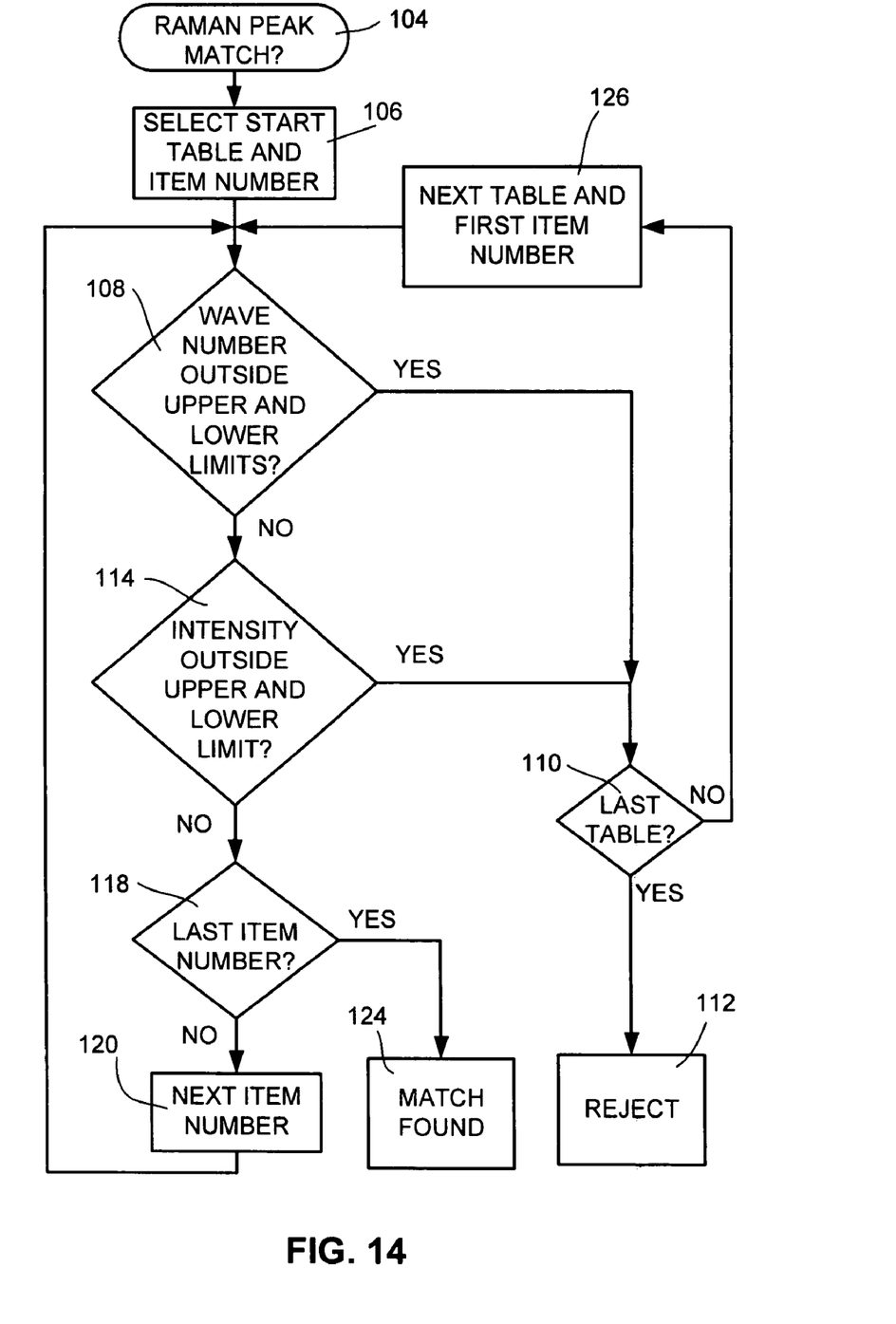
FIG. 14 is a step diagram of a procedure for comparing peak data of FIG. 12 with the Raman peak data in the library of FIG. 13.

Following determination of the peaks in the Raman spectrum, the program of FIG. 3 in step 104 performs a match determination procedure shown in FIG. 14. The Raman peak library shown in FIG. 13 contains tables (only one table with a few bins is shown in FIG. 13) each containing peak numbers, wave numbers, intensity values and standard deviations (values x1-x31 are determined from several readings of mark having the same DNA fragments) for peaks of Raman spectrum produced by the DNA in an authentic mark. In step 106 the start table and the data entry first peak in the start table are selected. In step 108 it is determined if the wave number of the current peak under examination is outside of upper and lower limits by an algorithm similar to that described above for fluorescence data; the standard deviation can be a set number for all the wave numbers in the table and so does not need to be set forth in the table. If the wave number is outside the upper and lower limits, step 110 branches to step 110 where it is determined if the current table is the last table in the Raman peak library. If true, the procedure indicates a rejection of the mark. When step 108 is false, step 114 determines if the intensity value is outside upper and lower limits by the comparing algorithm using the standard deviation set forth for the current data entry in the table. Again if the intensity is outside the permissible limits the procedure branches to step 110, otherwise step 118 determines if the current peak under consideration is the last peak to be considered and if false selects the next peak in step 120 and returns to step 108 to test this next peak. When step 110 finds that the current table is not the last table in the library, the program in step 126 selects the next library table and proceeds to step 108 to compare the current peaks under consideration with the newly selected table. When the testing reaches the last peak entry and it is found within the acceptable table values, the procedure indicates a match in step 124.

When the procedure of FIG. 14 returns a reject to the program of FIG. 3 the computer indicates in step 98 that the marked item under consideration is not authentic. Conversely if a match found is returned, the computer indicates in step 130 that the item is authentic.

The above detailed description and the accompanying drawings are only illustrative and many modifications, variations, alternatives and changes in detail can be employed without departing from the scope and spirit of the invention.

The invention claimed is:

1. A method of identifying items having a security mark containing a DNA fragment to prevent fraud comprising:
    using a Raman spectrometer to generate a response spectrum of a security mark on an item;
    removing gross fluorescence from the security mark response spectrum to produce a Raman security mark response spectrum;
    detecting peaks in the Raman security mark response spectrum to generate Raman security mark peak data;
    comparing the Raman security mark peak data to a Raman peak library to determine if there is a match; and
    indicating that the item is authentic if a match of the Raman security mark peak data is found in the Raman peak library by the comparing.

2. A method as defined in claim 1 including comparing the security mark response spectrum with a library of response spectrums of DNA fragments to determine if security mark response spectrum is acceptable prior to removing gross fluorescence from the security mark response spectrum.

3. A method as claimed in claim 2 wherein the comparing of the security marks response spectrum includes comparing intensity values with upper and lower limit values in the library of response spectrums.

4. A method as claimed in claim 3 wherein the removing of gross fluorescence is performed by determining an average value of intensity data within a section surrounding each point of the security mark response spectrum, and subtracting the average value from each point to produce the Raman security mark spectrum.

5. A method as claimed in claim 3 wherein the comparing of Raman peak data with the Raman peak library includes comparing wave numbers of each peak with wave numbers in the Raman peak library and comparing intensity values of each peak with intensity values in the Raman peak library.

6. A method as claimed in claim 2 wherein the removing of gross fluorescence is performed by determining an average value of intensity data within a section surrounding each point of the security mark response spectrum, and subtracting the average value from each point to produce the Raman security mark spectrum.

7. A method as claimed in claim 2 wherein the comparing of Raman peak data with the Raman peak library includes comparing wave numbers of each peak with wave numbers in the Raman peak library and comparing intensity values of each peak with intensity values in the Raman peak library.

8. A method as claimed in claim 1 wherein the removing of gross fluorescence is performed by determining an average value of intensity data within a section surrounding each point of the security mark response spectrum, and subtracting the average value from each point to produce the Raman security mark spectrum.

9. A method as claimed in claim 8 wherein the comparing of Raman peak data with the Raman peak library includes comparing wave numbers of each peak with wave numbers in the Raman peak library and comparing intensity values of each peak with intensity values in the Raman peak library.

10. A method as claimed in claim 1 wherein the comparing of Raman peak data with the Raman peak library includes comparing wave numbers of each peak with wave numbers in the Raman peak library and comparing intensity values of each peak with intensity values in the Raman peak library.

11. An apparatus for identifying items having a security mark containing a DNA fragment to prevent fraud comprising:
    a Raman spectrometer for generating a response spectrum from the security mark, and
    a computer for removing gross fluorescence from the security mark response spectrum to produce a Raman security mark response spectrum, detecting peaks in the Raman security mark response spectrum to generate Raman security mark peak data, comparing the Raman security mark peak data to a Raman peak library to determine if there is a match, and indicating that the item is authentic if a match of the Raman security mark peak data is found in the Raman peak library by the comparing.

12. An apparatus as claimed in claim 11 wherein the computer compares the security mark response spectrum with a library of response spectrums of DNA fragments to determine if security mark response spectrum is acceptable prior to removing gross fluorescence from the security mark response spectrum.

13. An apparatus as claimed in claim 12 wherein the computer compares the security marks response spectrum by comparing intensity values with upper and lower limit values in the library of response spectrums.

14. An apparatus as claimed in claim 11 wherein the computer removes gross fluorescence by determining an average value of intensity data within a section surrounding each point of the security mark response spectrum, and subtracting the average value from each point to produce the Raman security mark spectrum.

15. An apparatus as claimed in claim 11 wherein the computer compares the Raman peak data with the Raman peak library by comparing wave numbers of each peak with wave numbers in the Raman peak library and comparing intensity values of each peak with intensity values in the Raman peak library.

* * * * *